United States Patent
Ricciardi et al.

(10) Patent No.: US 6,204,028 B1
(45) Date of Patent: Mar. 20, 2001

(54) METHODS FOR IDENTIFYING ANTIVIRAL AGENTS AGAINST HUMAN HERPESVIRUSES

(75) Inventors: Robert P. Ricciardi, Glen Mills; Kai Lin, Glenolden, both of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/280,766

(22) Filed: Mar. 29, 1999

Related U.S. Application Data

(60) Provisional application No. 60/080,636, filed on Apr. 3, 1998.

(51) Int. Cl.⁷ .............................. C12P 19/34; C12Q 1/70; C12Q 1/68; C12N 9/00; C07H 21/04
(52) U.S. Cl. .............................. 435/91.33; 435/5; 435/6; 435/91.1; 435/91.2; 435/183; 536/23.72
(58) Field of Search ........................ 435/5, 6, 91.1, 435/91.2, 183, 235.1; 436/94; 536/23.1, 23.7, 24.33, 25.3

(56) References Cited

PUBLICATIONS

Digard et al., Specific inhibition of herpes simplex virus DNA polymerase by helical peptides corresponding to the subunit interface. Proc. Natl. Acad. Sci. USA 92, 1456–1460, Feb. 1995.*
Ablashi et al. *Human Herpesvirus–6. Perspectives in Medical Virology*, A.J. Zuckerman, Editor, 1992, vol. 4, Elsevier, Amsterdam.
Agulnick et al., "Identification of a DNA–binding protein of human herpevirus 6, a putative DNA polymerase stimulatory factor", *J. Gen. Virol.* 1993 74:1003–1009.
Braun et al., "Human Herpesvirus 6", *Clin. Microbiol. Rev.* 1997 10:521–567.
Brooks et al., "Kaposi's Sarcoma–Associated Herpesvirus (KSHV) /Human Herpesvirus 8 (HHV8)—A New Human Tumour Virus", *J. Pathol.* 1997 182:262–265.
*Methods in Molecular Medicine*, S. M. Brown and A. R. MacLean, Eds., Human Press Inc., Totowa, NJ, 1997, vol. 10: Herpes Simplex Virus Protocols.
Cesarman et al., "Kaposi's Sarcoma–Associated Herpesvirus–Like DNA Sequences in Aids–Related Body–Cavity–Based Lymphomas", *N. Engl. J. Med.* 1995 332:1186–1191.
Chang et al., "Identification of Herpesvirus–Like DNA Sequences in AIDS–Associated Kaposi's Sarcoma", *Science* 1994 266:1865–1869.
Corbelliono et al., "Disseminated human herpesvirus 6 infection in AIDS", *Lancet* 1993 342:1242.
Digard et al., "Functional Analysis of the Herpes Simplex Virus UL42 Protein", *J. Virol.* 1993 67:1159–1168.
Ertl, P.F. and Powell, K.L., "Physical and Functional Interaction of Human Cytomegalovirus DNA Polymerase and Its Accessory Protein (ICP36) Expressed in Insect Cells", *J. Virol.* 1992 66:4126–4133.
Gompels et al., "The DNA Sequence of Human herpesvirus–6: Structure, Coding Content, and Genome Evolution", *Virology* 1995 209:29–51.
Gottlieb et al., "The Herpes Simplex Virus Type 1 UL42 Gene Product: a Subunit of DNA Polymerase That Functions To Increase Processivity", *J. Virol.* 1990 64:5976–5987.
Gu et al., "Recombinant Proteins Attached to a Nickel–NTA Column:Use in Affinity Purification of Antibodies", *BioTechniques* 1994 17:257–262.
Johnson et al., "Isolation of a Herpes Simplex Virus Type 1 Mutant Deleted for the Essential UL42 Gene and Characterization of Its Null Phenotype", *J. Virol.* 1991 65:700–710.
Kiehl, A. and Dorsky, D.I., "Bipartite DNA–Binding Region of the Epstein–Barr Virus BMRF1 Product Essential for DNA Polymerase Accessory Function", *J. Virol.* 1995 69:1669–1677.
Knox, K.K. and Carrigan, D.R., "Disseminated active HHV–6 infections in patients with AIDS", *Lancet* 1994 343:577–578.
Kong et al., "Three–Dimensional Structure of the β Subunit of *E. Coli* DNA Polymerase III Holoenzyme: A Sliding DNA Clamp", *Cell* 1992 69:425–437.
Krishna et al., "Crystal Structure of the Eukaryotic DNA Polymerase Processivity Factor PCNA", *Cell* 1994 79:1233–1243.
Lai, J.–S. and Herr, W., "Ethidium bromide provides a simple tool for identifying genuine DNA–independent protein associations", *Proc. Natl. Acad. Sci. USA* 1992 89:6958–6962.
Levy, J. A., "Three new human herpesviruses (HHV6, 7, and 8)", *Lancet* 1997 349:558–563.
Lusso, P. and Gallo, R.C., "Human herpesvirus 6 in AIDS", *Immunol. Today* 1995 16:67–71.
Mocarski et al. "Precise localization of genes on large animal virus genomes: use of λgt and monoclonal antibodies to map the gene for a cytomegalovirus protein family", *Proc. Natl. Acad. Sci. USA* 1985 82:1266–1270.
Neipel et al., "Cell–Homologous Genes in the Kaposi's Sarcoma–Associated Rhadinovirus Human Herpesvirus 8: Determinants of Its Pathogenicity?", *J. Virol.* 1997 71:4187–4192.

(List continued on next page.)

Primary Examiner—Bradley L. Sisson
Assistant Examiner—Frank Lu
(74) Attorney, Agent, or Firm—Law Offices of Jane Massey Licata

(57) ABSTRACT

A method of screening compounds for antiviral activity against a selected human herpesvirus by measuring inhibition of DNA synthesis by DNA polymerase and processivity factor of the selected human herpesvirus in the presence of the compound is provided.

1 Claim, No Drawings

OTHER PUBLICATIONS

Rettig et al., "Kaposis's Sarcoma–Associated Herpesvirus Infection of Bone Marrow Dendritic Cells from Multiple Myeloma Patients", *Science* 1997 276:1851–1854.

Ripalti et al., "Cytomegalovirus–Mediated Induction of Antisense mRNA Expression to UL44 Inhibitis Virus Replication in an Astrocytoma Cell Line: Identification of an Essential Gene", *J. Virol.* 1995 69:2047–2057.

Said et al., "Localization of Kaposi's Sarcoma–Associated herpesvirus in Bone Marrow Biopsy Samples From Patients With Multiple Myeloma", *Blood* 1997 90:4278–4282.

Soulier et al., "Kaposi's Sarcoma–Associated Herpesvirus–Like DNA Sequences in Multicentric Castleman's Disease", *Blood* 1995 86:1276–1280.

Sun et al., "Polyadenylylated nuclear RNA encoded by Kaposi sarcoma–associated herpesvirus", *Proc. Natl. Acad. Sci. USA* 1996 93:11883–11888.

Teo et al., "Characterization of the DNA Polymerase Gene of Human Herpesvirus 6", *J. Virol.* 1991 65:4670–4680.

Tsurumi et al., "Functional Interaction between Epstein–Barr Virus DNA Polymerase Catalytic Subunit and Its Accessory Subunit In Vitro", *J. Virol.* 1993 67:7648–7653.

Weiland et al., "Functional analysis of human cytomegalovirus polymerase accessory protein", *Virus Res.* 1994 34:191–206.

* cited by examiner

US 6,204,028 B1

METHODS FOR IDENTIFYING ANTIVIRAL AGENTS AGAINST HUMAN HERPESVIRUSES

This application claims benefit of Provisional appl. No. 60/080,636, filed Apr. 3, 1998.

FIELD OF THE INVENTION

The present invention relates to a fast and convenient method that can be used to screen thousands of compounds for their potential to perturb or disrupt DNA synthesis by selected human herpesvirus polymerase/processivity factor proteins. The method of the present invention is useful in identifying potential antiviral agents against selected human herpesviruses including, but not limited to, human herpesvirus-8 and human herpesvirus-6.

BACKGROUND OF THE INVENTION

The first step in determining the potential antiviral activity of compounds is to use an initial or primary screen to identify whether a particular compound has some degree of antiviral activity. Since primary screening often involves large numbers of compounds, it is preferred that the assay system be automated to reduce human resources required and supply costs. Initial screens are typically kept quite simple, using a single method, one virus isolate for each virus group and a single cell line, preferably of human origin. Two basic types of screening assays have been used, depending upon whether the particular virus replicates in tissue culture cells and produces some type of cellular destruction or morphological change (cytopathic effect; CPE). For viruses that produce CPE, such as herpes simplex virus, the most commonly used assay systems are those that measure inhibition of CPE, focus formation, or syncytial formation. Nucleic acid hybridization is also used for viruses such as cytomegalovirus that may take a long time in culture to produce CPE, or for viruses such as Epstein Barr virus that do not produce CPE in cell culture systems but do replicate their DNA. Other assay systems that do not depend on complete viral replication with the production of CPE monitor synthesis of specific gene products such as P24 for HIV and enzymes such as thymidine kinase, DNA polymerase, or reverse transcriptase.

Human herpesvirus 6 (HHV-6) is the causative agent of roseola infantum, a common disease of infancy characterized by high fever and skin rash. This herpesvirus has also been suggested to have a role in mononucleosis, multiple sclerosis, pneumonitis and bone marrow suppression in transplant rejections (Ablashi et al. *Human Herpesvirus-6. Perspectives in Medical Virology*, A. J. Zuckerman, Editor, 1992, Vol. 4, Elsevier, Amsterdam; Braun et al. *Clin. Microbiol. Rev.* 1997 10:521–567). HHV-6 is tropic for CD4+ T cells, which are also the natural targets for HIV infectivity. Thus, in AIDS patients, HHV-6 may contribute to the attrition of T cells, which is consistent with its potential catalytic role in HIV infection (Ablashi et al. *Human herpesvirus-6. Perspectives in Medical Virology*. A. J. Zuckerman, Editor, 1992, Vol.4. Elsevier, Amsterdam.; Braun et al. *Clin. Microbiol. Rev.* 1997 10:521–567; Lusso, P. and Gallo, R. C. *Immunol. Today* 1995 16:67–71) and its actual detection in many different necropsied tissues (Corbelliono et al. *Lancet* 1993 342:1242; Knox, K. K. and Carrigan, D. R. *Lancet* 1994 343:577–578). HHV-6 has a linear DNA genome of 160 kbp which is now completely sequenced (Gompels et al. *Virology* 1995 209:29–51); there are 119 open reading frames predicted, of which 67% have counterparts in human cytomegalovirus (HCMV). Although certain structural and functional genes have been identified (Braun et al. *Clin. Microbiol. Rev.* 1997 10:521–567), little is known about the nature of many HHV-6 gene products and the manner in which the virus is regulated.

Human herpesvirus-8 (HHV-8) is a recently identified herpesvirus which is the apparent causative factor of Kaposil's sarcoma, the most common neoplasm of AIDS patients (Chang et al. *Science* 1994 266:1865–1869). Accordingly, HHV-8 is oftentimes referred to as Kaposils sarcoma-associated herpesvirus (KSHV). KSHV is also found in Kaposi's sarcoma tumors of non-AIDS patients. The causative role of KSHV in formation of these neoplasms is strongly supported by seroconversion to viral antigens prior to the clinical appearance of Kaposi's sarcoma. KSHV is also associated with body cavity based lymphoma or pleural effusion lymphoma (Cesarman et al. *N. Engl. J. Med.* 1995 332:1186–1191) and multicentric Castleman's disease (Soulier et al. *Blood* 1995 86:1276–1280). In Kaposi's sarcoma and pleural effusion lymphoma, malignant cells harbor the virus. Recently, KSHV was suggested to be involved in the bone marrow cancer, multiple myeloma and monoclonal gammopathy of undetermined significance (Rettig et al. *Science* 1997 276:1851–1854; Said et al. *Blood* 1997 90:4278–4282; Brooks et al. *J. Pathol.* 1997 182:262–265; Levy. J. A. *Lancet* 1997 349:558–563; Neipel et al. *J. Virol.* 1997 71:4187–4192).

Accordingly, there is a need for rapid screening methods to identify potential antiviral agents specific against these and other human herpesviruses.

SUMMARY OF THE INVENTION

An object of the present invention is to provide a method of screening compounds to identify potential antiviral agents against a selected herpesvirus which comprises measuring DNA synthesis by DNA polymerase and processivity factor of the selected human herpesvirus in the absence and presence of a compound wherein inhibition of DNA synthesis in the presence of the compound is indicative of antiviral activity against the selected human herpesvirus.

DETAILED DESCRIPTION OF THE INVENTION

Processivity factors associate with certain DNA polymerases, allowing them to synthesize extended stretches of DNA without dissociating from the template. Two such well-studied proteins, PCNA (proliferating cell nuclear antigen) of yeast and the β subunit of *Escherichia coli* (*E. coli*) DNA polymerase III holoenzyme, have been crystallized (Kong et al. *Cell* 1992 69:425–437; Krishna et al. *Cell* 1994 79:1233–1243). They confer processivity by forming topological rings encircling duplex DNA that tether their polymerases and slide along the DNA template. Several herpesvirus processivity factors have been identified, including UL42 of herpes simplex virus type 1 (HSV-1) (Gottlieb et al. *J. Virol.* 1990 64:5976–5987), BMRF1 of Epstein-Barr virus (EBV) (Kiehl, A. and Dorsky, D. I. *J. Virol.* 1995 69:1669–1677; Tsurumi et al. *J. Virol.* 1993 67:7648–7653), and ICP36 of HCMV (Ertl, P. F. and Powell, K. L. *J. Virol.* 1992 66:4126–4133; Mocarski et al. *Proc. Natl. Acad. Sci. USA* 1985 82:1266–1270; and Weiland et al. *Virus Res.* 1994 34:191–206). While the structure and mechanism by which these viral proteins confer processivity upon their polymerases remains unclear, herpesvirus processivity factors have been shown to be critical for viral replication (Johnson et al. *J. Virol.* 1991 65:700–710; Ripalti et al. *J. Virol.* 1995

69:2047–2057). Significantly, the UL42 null HSV-1 mutant failed to infect and replicate in Vero cells (Johnson et al. *J. Virol.* 1991 65:700–710). Also, an antisense mRNA targeted against ICP36 strongly inhibited CMV replication (Ripalti et al. *J. Virol.* 1995 69:2047–2057).

The 41 kD early antigen of human herpesvirus 6 (HHV-6), which exhibited nuclear localization and DNA-binding activity (Agulnick et al. *J. Gen. Virol.* 1993 74:1003–1009) has now been confirmed to co-immunoprecipitate with a 110 kD protein identified to be the HHV-6 DNA polymerase (Pol-6) by an antibody raised against Pol-6. Co-immunoprecipitation experiments using anti-p41 and anti-Pol-6 antibodies confirmed that p41 complexed with Pol-6 in HHV-6 infected cells. In addition, both p41 and Pol-6 were synthesized in vitro and shown to form a specific complex. An in vitro polymerase assay using primed M13 single-stranded DNA template demonstrated that p41 functions as the processivity factor of HHV-6. Not only did p41 greatly increase the DNA synthesis activity of Pol-6, it allowed Pol-6 to synthesize DNA products corresponding to full-length M13 template (7,249 nucleotides), whereas Pol-6 alone could only synthesize DNA of less than 100 nucleotides. Moreover, the functional interaction between Pol-6 and p41 appears to be specific, since they failed to be physically or functionally substituted in vitro by herpes simplex virus 1 homologues.

The processivity factor (PF-8) and DNA polymerase (Pol 8) of human herpes virus-8 (HHV-8/KSHV) have also now been cloned and expressed. Pol-8 binds specifically to PF-8 in vitro. Moreover, the DNA synthesis activity of Pol-8 was shown in vitro to be strongly dependent on PF-8. Addition of PF-8 to Pol-8 allowed efficient synthesis of fully extended DNA products corresponding to the full-length M13 template (7,249 nucleotides), whereas Pol-8 alone could incorporate only several nucleotides. The specificity of PF-8 and Pol-8 for each other was demonstrated by their inability to be functionally substituted by the DNA polymerases and processivity factors of herpes simplex virus 1 and human herpesvirus 6.

It is believed that the targeted disruption of this interaction of a selected human herpesvirus DNA polymerase with its processivity factor by selected or designed inhibitors will lead to an effective anti-viral strategy against specific human herpesvirus. In the present invention, a method is provided for rapid screening of compounds to identify those compounds which perturb or disrupt DNA synthesis by selected human herpesvirus polymerase/processivity factor proteins.

In a preferred embodiment, the high throughput method of the present invention is conducted in 96 well microtiter plates. Each individual reaction well in the 96-well plate contains all the components necessary to permit detection of the DNA polymerase/processivity factor dependent synthesis of DNA. Specifically, a single stranded template DNA of a defined length, preferably from about 50 to about 500 nucleotides, is immobilized to each well. Methods of immobilizing DNA to a solid support are well known in the art and include, for example, conjugating the oligonucleotide to biotin and coating the solid support with streptavidin or avidin. An oligonucleotide primer is annealed to the 3' end of the immobilized DNA template. A radioactive-labeled dNTP or a nonradioactive-labeled dNTP such as digoxigenin-dUTP (1:20, dig-dUTP:dTTP) as well as the four deoxynucleotides at concentrations that permit optimal incorporation are also included in each well. Addition of an HHV DNA polymerase and its processivity factor, preferably Pol-8 and PF-8 or Pol-6 and p41, result in the incorporation of these dNTPs as well as the labeled UTP. Newly synthesized DNA is then detected radiometrically or colorimetrically via an agent which detects the nonradioactive-labeled dNTP such as an anti-digoxigenin-antibody conjugate, for example, peroxidase-conjugated anti-digoxigenin antibody or alkaline phosphatase-conjugated anti-digoxigenin antibody. Compounds which inhibit DNA synthesis are identified by a decrease or absence in color as compared to controls wells which do not contain the compound. Such compounds are potential antiviral agents for the herpesvirus to which the DNA polymerase and processivity are specific for. The ability of compounds identified by the screening method of the present invention to be potential antiviral agent to inhibit viral propagation is then confirmed in cells infected with the herpesvirus.

The following nonlimiting examples are provided to further illustrate the present invention.

EXAMPLES

Example 1

Identification of HHV-6 DNA Polymerase and Processivity Factor

Cell Lines and Viruses

Two T cell lines, J-Jhan and Molt-3, were propagated at 37° C. in RPMI-1640 medium (Gibco) containing 10% fetal bovine serum (FBS, Hyclone). J-Jhan and Molt-3 were infected by HHV-6 strains, GS and Z-29, respectively. Continuous infected cultures were maintained by adding infected T cells, exhibiting 80% cytopathic effect, to uninfected T cells, at a ratio of 1:5. Spodoptera frugiperda (Sf9) cells were grown as described by Willis et al. "Expression and purification of secreted forms of HSV glycoproteins from baculovirus-infected insect cells", *Methods in Molecular Medicine*, S. M. Brown and A. R. MacLean, Eds., Human Press Inc., Totowa, N.J., 1997, Vol 10: Herpes Simplex Virus Protocols.

Plasmid Constructs

The HHV-6 DNA polymerase (Pol-6) gene was amplified from a HHV-6 genomic DNA clone, pRPM4.4 (Teo et al. *J. Virol.* 1991 65:4670–4680), by PCR using two oligonucleotides, N-Pol (5'-CGCGCGCCATGGATTCGGTGTCG-3'; SEQ ID NO: 1) and C-Pol (5'-GCGCGAATTCCATTCACATTACCTCTGC-3'; SEQ ID NO: 2), to create a NcoI site flanking the 5' end and an EcoRI site flanking the 3' end of the Pol-6 coding region, respectively. To construct pTM1-Pol-6, the amplified Pol-6 gene was cloned into the NcoI and EcoRI sites of the in vitro transcription/translation vector pTM1. To construct pAcHLT-Pol-6, Pol-6 gene was cloned from pTM1-Pol-6 into the NcoI and SacI sites of the baculovirus transfer vector pAcHLT-B (Invitrogen). The plasmid pET-PolN, encoding the N-terminal 159 amino acids of Pol-6, was generated by subcloning the coding region between NcoI and PstI sites of pTM1-Pol-6 into pET-21b vector (Novagen). To construct pTM1-p41, a pBluescript plasmid containing the HHV-6 p41 gene (Agulnick et al. *J. Gen. Virol.* 1993 74:1003–1009) was amplified by PCR using two oligonucleotides, N-p41 (5'-CTATCCATGGAGCGCGGTAGTC-3'; SEQ ID NO: 3) and C-p41 (5'-CAGAATTCAGACGACGCATCTC-3'; SEQ ID NO: 4), to create a NcoI site flanking the 5' end and a EcoRI site flanking the 3' end of the p41 coding region, respectively. The amplified p41 gene was cloned into the NcoI and EcoRI sites of pTM1. All the plasmid constructs were introduced into *E. coli* DH5α (Gibco).

Antibodies

The N-terminal 159 amino acid coding region of Pol-6, cloned into the expression vector pET-PolN which supplies an C-terminal 6xHis tag, was over-expressed in *E. coli* by induction with 1 mM isopropyl-β-D-thiogalactopyranoside (IPTG). The 6xHis-PolN protein was purified by Clontech TALON metal affinity resin, dialyzed against PBS containing 10% glycerol and 8 M urea, and used to generate a rabbit polyclonal antiserum, Pol6N159 (Cocalico). The antiserum was purified by an antigen affinity column, which was generated by coupling 6xHis-PolN protein to a QIAGEN Ni2+-NTA agarose column (Gu et al. *BioTechniques* 1994 17:257–262.). The mouse monoclonal antibody which recognizes the HHV-6 p41 protein was 9A5D12 (tissue culture supernatant).

Expression of Pol-6 in Sf9 Cells

A recombinant baculovirus was generated by co-transfection of pAcHLT-Pol-6, which supplied a 6xHis tag to the N-terminus of the Pol-6 gene, and BaculoGold linear DNA (Pharmingen) into Sf9 cells. The 6xHis recombinant Pol-6 protein (baculo-Pol-6) was over-expressed in Sf9 cells, and purified by a $Ni^{2+}$-NTA Agarose column (QIAGEN).

Western Blot Analysis

Cell extracts or proteins were fractionated on 4–20% SDS polyacrylamide gels (BioRad) and electrophoretically transferred to Millipore Immobilon-P Transfer Membranes. To detect p41, the blot was incubated with 9A5D12 (1:10 dilution) for 2 hours, then with goat anti-mouse IgG-HRP (Boehringer-Mannheim) for 1 hour. To detect Pol-6, the blot was incubated with affinity purified Pol6N159 (1:500 dilution), then with goat anti-rabbit IgG-HRP. The blots were visualized by enhanced chemiluminescence (Amersham).

Radiolabeling of Cells

Uninfected or HHV-6 infected T cells ($10^7$) were washed with RPMI (-Met, GIBCO) twice, then labeled in RPMI (-Met) containing 250 μCi L- [$^{35}$S]-methionine (>1000 Ci/mmol, Amersham) and 10% dialyzed FBS for 24 hours.

Immunoprecipitation

Uninfected or HHV-6 infected T cells ($10^7$) were lysed in 1 ml Buffer A (50 mM Tris-HCl, 150 mM NaCl, and 1% NP-40) on ice for 30 minutes. The cell lysates were incubated with either 50 μl anti-p41antibody (9A5D12) or 1 μg purified anti-Pol-6 antibody (Pol6N159) for 2 hours, then with 20 μl Protein A-Sepharose (Pharmacia) for 1 hour at 4° C. After washing extensively with Buffer A, the immunoprecipitates were eluted by boiling in Laemmli buffer and fractionated on 4–20% SDS polyacrylamide gels.

In Vitro Transcription/Translation

Both unlabeled and [$^{35}$S]-methionine labeled proteins were synthesized in vitro using the Promega TNT coupled reticulocyte lysate systems. Pol-6 and p41 were transcribed/translated from pTM1-Pol-6 and pTM1-p41, respectively, using T7 RNA polymerase TNT system. HSV-1 UL30 and UL42 were transcribed/translated from p911 and pINGUL42ΔMCS, respectively, using T3 or SP6 RNA polymerase TNT system.

In Vitro Binding Assay

Individual or combined in vitro translated proteins were incubated with either 40 μl anti-p41 antibody (9A5D12) or 1 μg purified anti-Pol-6 antibody (Pol6N159) at 4° C. for 2 hours in the presence of 100 mM KCl, 5 mM $MgCl_2$, and 50 mM Tris-HCl (pH 7.6), and 0.1% NP-40, and then with 20 μl Protein A-Sepharose at 4° C. for 1 hour. After washing extensively with a buffer containing 100 mM KCl, 5 mM $MgCl_2$, and 50 mM Tris-HCl (pH 7.6), and 1% NP-40, the immunoprecipitates were eluted by boiling in Laemmli buffer and fractionated on 4–20% SDS polyacrylamide gels.

In Vitro DNA Synthesis Assays

In vitro DNA synthesis assays were performed essentially as described by Digard et al. *J. Virol.* 1993 67:1159–1168. M13 primed template was prepared by annealing M13 Universal sequencing primer to M13mp18(+) single-stranded DNA (Pharmacia) in the presence of 100 mM NaCl, 1 mM EDTA, and 50 mM Tris-Cl (pH 7.6). Excess primer was removed by filtration through a Centricon-100 spin filter (Amicon). For each 50 μl reaction, 5 μl of each in vitro translated protein was added to a buffer containing 100 mM $(NH_4)_2SO_4$, 20 mM Tris-Cl (pH 7.5), 3 mM $MgCl_2$, 0.1 mM EDTA, 0.5 mM dithiothreitol, 4% glycerol, 40 mg/ml bovine serum albumin, 60 μM each of dATP, dGTP, and dTTP, 10 μM [α-$^{32}$P]-dCTP (3000 Ci/mmol, NEN), and 50 fmol of M13 primed template and incubated at 37° C. for 30 minutes.

To measure the incorporation of [α-$^{32}$P]-dCTP, 5 μl of each reaction was mixed with 50 μl of ice-cold 5% trichloroacetic acid (TCA) and 20 mM sodium pyrophosphate for 10 minutes, loaded on a Whatman GF/A glass fiber filter which was then washed extensively with 5% TCA and 20 mM sodium pyrophosphate, and followed by a final rinse with 70% ethanol. The filters were dried and counted by a Beckman liquid scintillator LS2800.

To determine the length of labeled DNA products synthesized, the remainder of the reaction was incubated at 37° C. for 1 hour with 50 μl 1% SDS, 10 mM EDTA, 10 mM Tris-Cl (pH 8), and 200 μg/ml proteinase K, followed by phenol/chloroform extraction. The synthesized DNA products were ethanol precipitated in the presence of 1 M ammonium acetate, resuspended in 50 μl gel loading buffer (50 mM NaOH, 2.5 mM EDTA, 25% glycerol, and 0.025% bromocresol green) and then fractionated on a 1.3% alkaline agarose gel. The gel was dried and subject to autoradiography or analysis by PhosphorImager (Molecular Dynamics).

Example 2

Identification of HHV-8 DNA Polymerase and Processivity Factor

Cloning of Pol-8 and PF-8

Two genomic DNA clones of KSHV (Sun et al. *Proc. Natl. Acad. Sci. USA* 1996 93:11883–11888), GB11 containing ORF9 and GB21 containing ORF59, were used to clone Pol-8 and PF-8, respectively. The 3,038 bp Pol-8 gene was amplified from GB11 by PCR using two primers, N-Pol (5'-ATTACCATGGATTTTTTCAATCCATTTA-3'; SEQ ID NO: 5) creating a NcoI site flanking the 5' end, and C-Pol (5'-ATAAGAGCTCTAGGGCGTGGGAAAAG-3'; SEQ ID NO: 6) creating a SacI site flanking the 3' end of the Pol-8 coding region. The 1,190 bp PF-8 gene was amplified from GB21 by PCR using two primers, N-PF (5'-TATTCCATGGTAATGCCTGTGGATTTTCACT-3'; SEQ ID NO: 7) creating a NcoI site flanking the 5' end, and C-PF (5'-TATAGAGCTCAAATCAGGGGGTTAAATG-3'; SEQ ID NO: 8) creating a SacI site flanking the 3' end of the PF-8 coding region. Both of the genes were cloned into the NcoI and SacI sites of the pTM1 expression vector and their ORFs were confirmed by DNA sequencing. Proteins were synthesized in vitro using the Promega T7-TNT coupled reticulocyte lysate system. A protein of approximately 114 kD corresponding to the predicted 1,012 amino acid ORF of Pol-8 was synthesized from pTM1-Pol-8, and a protein of approximately 50 kD corresponding to the predicted 396 amino acid ORF of PF-8 was synthesized from pTM1-PF-8.

GST Binding Assay

A GST-binding assay was employed to determine if Pol-8 and PF-8 form a specific complex in vitro. The full-length PF-8 gene was subcloned from pTM1-PF-8 into the EcoRI and NotI sites of a GST vector, pGEX4T-2 (Pharmacia). A GST-PF-8 fusion protein was over-expressed in *E. coli* and purified using glutathionine beads. For the GST-binding assay, 200 ng of either GST or GST-PF-8 fusion protein was incubated with 5 μL of [$^{35}$S]-methionine labeled in vitro translated Pol-8 at 30° C. for 1 hour, and then with 50 μl glutathione beads for 30 minutes in the presence of 0.1% NP-40, 100 mM KCl, 5 mM MgCl$_2$, and 50 mM Tris-Cl (pH 7.6). The beads were washed 3 times with 1% NP-40, 0.5 M KCl, 5 mM MgCl$_2$, and 50 mM Tris-HCl (pH 7.6), and then 3 times with 1% NP-40, 0.5% DOC, 0.1% SDS, 100 mM KCl, 5 mM MgCl$_2$, and 50 mM Tris-HCl (pH 7.6). Bound proteins were eluted by boiling in Laemmli buffer, then fractionated on a 4–20% SDS-polyacrylamide gel (BioRad) and examined by autoradiography. Ethidium bromide (200 μg/ml) was included in both binding and washing buffers to verify that this interaction was not mediated by the DNA contained in the transcription/translation reaction (Lai, J. -S. and Herr, W. *Proc. Natl. Acad. Sci. USA* 1992 89:6958–6962).

To demonstrate the specificity of the Pol-8/PF-8 interaction, the DNA polymerase of HSV-1 (UL30) was tested for its ability to complex with GST-PF-8. UL30 was unable to bind to GST-PF-8 under the same conditions in which Pol-8 bound to GST-PF-8.

In Vitro DNA Synthesis Assay

To investigate whether the interaction between Pol-8 and PF-8 is functionally significant, the DNA synthesis activity of Pol-8 in the absence or presence of PF-8 was determined by an in vitro DNA synthesis assay using primed M13 ssDNA as the template. The primed template was prepared by annealing M13 universal sequencing primer to M13mp18 (+) ssDNA (Pharmacia) in the presence of 100 mM NaCl, 1 mM EDTA, and 50 mM Tris-Cl (pH 7.6). Excess primer was removed by filtration through a Centricon-100 spin filter (Amicon). For the DNA synthesis assay, 2 μl (unless indicated otherwise) of each in vitro translated protein was included in a 25 μl reaction containing 100 mM (NH$_4$)$_2$SO$_4$, 20 mM Tris-Cl (pH 7.5), 3 mM MgCl$_e$ 0.1 mM EDTA, 0.5 mM dithiothreitol, 4% glycerol, 40 μg/ml bovine serum albumin, 60 μM each of dATP, dGTP, and dTTP, 10 μM [α-$^{32}$P]-dCTP (3000 Ci/mmol, NEN), and 25 fmol of primed M13 ssDNA template. After incubation for 1 hour (unless indicated otherwise) at 37° C., the reactions were terminated by incubating at 37° C. for 1 hour with 50 μl of 1% SDS, 10 mM EDTA, 10 mM Tris-Cl (pH 8), and 200 μg/ml proteinase K, followed by phenol/chloroform extraction. The reactions were analyzed for either polymerase activity by measuring incorporation of dNTPs into the DNA products, or for processivity by measuring the length of newly synthesized DNA strands.

To determine the incorporation of [α-32P]-dCTP into synthesized DNA, 5 μl of each reaction was precipitated on ice for 10 minutes with 50 μl of 5% trichloroacetic acid (TCA)/20 mM sodium pyrophosphate, then captured on a Whatman RF/A glass fiber filter. The filter was washed extensively with 5% TCA/20 mM sodium pyrophosphate, rinsed with 70% ethanol, dried, and counted in a Beckman liquid scintillator LS2800.

To analyze the processivity of DNA synthesis, the length of the DNA products from the DNA synthesis assay was determined. The DNA products were ethanol precipitated in the presence of 1 M ammonium acetate and resuspended in 50 μl gel loading buffer (50 mM NaOH, 2.5 mM EDTA, 25% glycerol, and 0.025% bromocresol green), then fractionated on a 1.3% alkaline agarose gel. The gel was dried and examined by autoradiography.

To examine the specificity of Pol-8 and PF-8, these KSHV proteins were tested for their ability to function with HSV-1 DNA polymerase (UL30) and its processivity factor (UL42) in the DNA synthesis assay.

DNA synthesis activity of Pol-8 alone was also examined at a higher resolution. These DNA synthesis assays were performed as described above except that the primer was labeled at the 5' end with [α-$^{32}$P]-ATP and annealed to M13 ssDNA template, and various combinations of unlabeled dNTPs were used in the reaction. The synthesized DNA products were fractionated on a 15% urea-polyacrylamide gel, and examined by autoradiography.

What is claimed is:

1. A method of screening compounds in vitro for antiviral activity against a human herpesvirus 6 (HHV-6) or a human herpesvirus 8 (HHV-8) comprising:

(a) selecting the human herpesvirus to be a target for antiviral activity wherein said selected human herpesvirus is selected from the group consisting of HHV-6 or HHV-8;

(b) immobilizing a DNA of the selected human herpesvirus to a solid support;

(c) contacting the DNA of the human herpesvirus with a corresponding human herpesvirus DNA polymerase and a corresponding human herpesvirus processivity factor;

(d) detecting newly synthesized DNA in the presence and absence of a compound to be tested for antiviral activity wherein inhibition of DNA synthesis in the presence of the compound is indicative of antiviral activity against the human herpesvirus; and (e) repeating steps (a) through (d) in the presence and absence of the DNA polymerase and the combination of the DNA polymerase and the DNA processivity factor.

* * * * *

UNITED STATES PATENT AND TRADEMARK OFFICE
CERTIFICATE OF CORRECTION

PATENT NO.   : 6,204,028 B1
DATED        : March 20, 2001
INVENTOR(S)  : Ricciardi et al.

It is certified that error appears in the above-identified patent and that said Letters Patent is hereby corrected as shown below:

Column 2,
Line 7, please delete "Kaposil's" and insert -- Kaposi's --.

Column 5,
Line 38, please delete "250$\mu$CiI" and insert -- 250$\mu$CiL --.

Column 8,
Line 2, please delete "3 mM MgCl$_e$" and insert -- 3 mM MgCl$_2$ --.

Signed and Sealed this

Eleventh Day of March, 2003

JAMES E. ROGAN
*Director of the United States Patent and Trademark Office*

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:Synthetic

<400> SEQUENCE: 1
cgcgcgccat ggattcggtg tcg                                    23

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:Synthetic

<400> SEQUENCE: 2

```
gcgcgaattc cattcacatt acctctgc                              28

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:Synthetic

<400> SEQUENCE: 3
ctatccatgg agcgcggtag tc                                    22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:Synthetic

<400> SEQUENCE: 4
cagaattcag acgacgcatc tc                                    22

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:Synthetic

<400> SEQUENCE: 5
attaccatgg attttttcaa tccattta                              28

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:Synthetic

<400> SEQUENCE: 6
ataagagctc tagggcgtgg gaaaag                                26

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence:Synthetic

<400> SEQUENCE: 7
tattccatgg taatgcctgt ggattttcac t                          31

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence:Synthetic

<400> SEQUENCE: 8
tatagagctc aaatcagggg gttaaatg                              28
```